United States Patent
Akamatsu et al.

(10) Patent No.: US 8,746,054 B2
(45) Date of Patent: Jun. 10, 2014

(54) PEEL TESTER, METHOD FOR EVALUATING IMPACT PEEL CHARACTERISTICS, ADHESIVE TAPE AND MOBILE DEVICE

(75) Inventors: Hideki Akamatsu, Ibaraki (JP); Kaori Numa, Ibaraki (JP); Yasunori Sugihara, Ibaraki (JP); Junji Yoshida, Ibaraki (JP)

(73) Assignee: Nitto Denko Corporation, Ibaraki-shi (JP)

( * ) Notice: Subject to any disclaimer, the term of this patent is extended or adjusted under 35 U.S.C. 154(b) by 696 days.

(21) Appl. No.: 12/989,499

(22) PCT Filed: May 8, 2009

(86) PCT No.: PCT/JP2009/058692
§ 371 (c)(1),
(2), (4) Date: Oct. 25, 2010

(87) PCT Pub. No.: WO2009/136635
PCT Pub. Date: Nov. 12, 2009

(65) Prior Publication Data
US 2011/0037687 A1   Feb. 17, 2011

(30) Foreign Application Priority Data
May 9, 2008 (JP) .................................. 2008-123656

(51) Int. Cl.
*G01N 19/04* (2006.01)
(52) U.S. Cl.
USPC .................... 73/150 A; 73/12.13; 73/12.06
(58) Field of Classification Search
USPC ............... 73/827, 150 A, 842, 12.06, 12.13
See application file for complete search history.

(56) References Cited

U.S. PATENT DOCUMENTS

2009/0211354 A1 * 8/2009 Lambert et al. ............. 73/150 A

FOREIGN PATENT DOCUMENTS

| JP | 2006-010931 A | 1/2006 |
| JP | 2006-225611 A | 8/2006 |
| JP | 2009-508099 A | 2/2009 |
| WO | WO 2004023111 A1 * | 3/2004 |
| WO | WO 2004109258 A1 * | 12/2004 |
| WO | 2007/028949 A1 | 3/2007 |

OTHER PUBLICATIONS

International Search Report of PCT/JP2009/058692, mailing date Jul. 21, 2009.
International Preliminary Report on Patentability (Form PCT/IB/373) of International Application No. PCT/JP2009/058692 dated Nov. 9, 2010 with Form PCT/ISA/237.

* cited by examiner

*Primary Examiner* — Hezron E Williams
*Assistant Examiner* — Paul West
(74) *Attorney, Agent, or Firm* — Westerman, Hattori, Daniels & Adrian, LLP (57) ABSTRACT

An object is to provide a peel tester that continuously detects the characteristics of an adhesive tape from the moment an impact is applied to an adherend until the adherend is peeled, and a new method for evaluating the impact peel characteristics of an adhesive tape, which enables quantitative evaluation for the impact peel characteristics by using the test result obtained by the peel tester. Provided is a peel tester 1 with a main body 2, to which an adherend I is to be adhered via an adhesive tape III, for performing a peel test by an impact applied to the adherend I, which includes: a load detection device 6 that detects change in load applied to the adhesive tape I until the adherend I is peeled off from the main body 2; and a displacement detection device 7 that detects change in moving distance of the adherend I until the adherend I is peeled off from the main body 2.

7 Claims, 9 Drawing Sheets

PEEL TESTER, METHOD FOR EVALUATING IMPACT PEEL CHARACTERISTICS, ADHESIVE TAPE AND MOBILE DEVICE

FIELD OF THE INVENTION

The present invention relates to a device for use in evaluating the peel characteristics of an adhesive tape by an impact and its evaluation method, and relates to an adhesive tape and a mobile device.

RELATED ART

Hitherto, an evaluation of the peel characteristics of an adhesive tape is performed by a dynamic evaluation method for evaluating the stress at the time when an adhesive tape is peeled off from an adherend on which the adhesive tape is adhered, a static evaluation method for evaluating the change with time of an adhesive tape kept adhered to an adherend, or the like. For example, as a dynamic evaluation method, a method for evaluating the stress (adhesive power) at the time when one end of a strip or band-shaped adhesive tape with an opposite end adhered to an adherend is pulled away from the adherend at a predetermined speed is used. This evaluation method is known as a 90 degree peel test for measuring the stress at the time when the one end of the adhesive tape is pulled away from the adherend in a direction 90 degrees from the surface of the adherend with the opposite end of the adhesive tape adhered thereto, or a 180 degree peel test for measuring the stress at the time when an adhesive tape is folded back at 180 degrees to have the one end pulled away towards the opposite end.

As a static evaluation method, a method for evaluating retention force by evaluating stability against time of an adhesive tape kept adhered to an adherend is known. Specifically, a method for evaluating positional displacement (moving distance) of the adhesive tape relative to the adherend or a method for evaluating the time until the adhesive tape is peeled off are used by adhering one end of an adhesive tape to an adherend, and, while subjecting the opposite end thereof to a predetermined load, leaving the adhesive tape for a predetermined time.

Furthermore, in these days, along with increase in demand for adhesive tapes for use in mobile devices, a demand for evaluation of the peel characteristics of an adhesive tape by an impact at the time when a mobile device is dropped (impact peel characteristics) exists. The evaluation of the impact peel characteristics is to evaluate the peel characteristics of an adhesive tape caused due to instantaneous load applied to the adhesive tape, and therefore this evaluation can be made by neither the above described dynamic nor static evaluation method. Thus, this evaluation was made by a different evaluation method.

Specifically, a method involves dropping a rigid body making the same collide with a test instrument having an adherend adhered thereto via an adhesive tape so as to apply instantaneous load onto the adherend by this impact. The test instrument has an impact surface, with which the dropped rigid body collides, on an upper side, and an adhering surface, to which an adherend is adhered via an adhesive tape, on a lower side opposite to the impact surface. By dropping the rigid body from above the region where the adherend is adhered and making the same collide with the impact surface, an evaluation is made to evaluate the peeling state of the adherend (whether the adherend has been peeled off or not) by an impact from a predetermined height, or an evaluation is made to evaluate the dropping height of a rigid body at the time when an adherend has been peeled off (cf. Patent Document 1).

PRIOR ART DOCUMENTS

Patent Document

Patent Document 1: Japanese Patent Application Laid-open No. 2006-10931

DISCLOSURE OF THE INVENTION

Problems to be Solved by the Invention

The evaluation method for evaluating the impact peel characteristics as described above is a method which involves evaluating whether an adherend has been peeled off or not by an impact of a dropped rigid body from a predetermined height, or a method which involves stepwisely varying the dropping height of a rigid body until an adherend is peeled off. Although these methods are effective as practical trials, they are hardly said to be quantitative evaluation methods. Thus, as a method for evaluating what characteristics an adhesive tape is to possess relative to instantaneous load caused by an impact, these methods are not appropriate.

It is an object of the present invention to provide a peel tester that continuously detects the characteristics of an adhesive tape from the moment an impact is applied to an adherend until the adherend is peeled off, and a new method for evaluating the impact peel characteristics of an adhesive tape, which enables quantitative evaluation on the impact peel characteristics by using the test result obtained by the peel tester. It is another object of the present invention to provide an adhesive tape subjected to a test by the peel tester, and a mobile device with a liquid crystal display part fixed in position by the adhesive tape.

Means for Solving Problems

According to the present invention, there is provided a peel tester with a main body, to which an adherend is to be adhered via an adhesive tape, for performing a peel test by an impact applied to the adherend, which includes: a load detection device that detects change in load applied to the adhesive tape until the adherend is peeled off from the main body; and a displacement detection device that detects change in moving distance of the adherend until the adherend is peeled off from the main body.

With the peel tester having the above structure including the load detection device that detects change in load applied to an adhesive tape, it is possible to continuously detect change in load from the moment the load is applied to the adherend until the adherend is peeled off. For example, in a peel test performed to peel off an adherend by an impact resulting from a collision of a rigid body, even when an instantaneous impact due to the collision of the rigid body took place, it is possible to continuously detect change in load applied to the adhesive tape from the moment of collision of the rigid body until peeling off of the adherend.

With the displacement detection device that detects change in moving distance of the adherend, it is possible to continuously detect change in moving distance of the adherend from the state where the adherend is kept adhered to the main body until the adherend is peeled off therefrom. For example, in a peel test performed to peel off an adherend by an impact resulting from a collision of the rigid body, the adherend is moved in a direction in which the impact is applied to the adherend (the direction in which the rigid body is dropped), and then is peeled off from the main body. At this moment, it is possible to continuously detect how far the adherend has moved from the adhered position on the main body until peeling off.

The peel tester of the present invention preferably further includes a peel device that is brought into contact with the adherend to peel off the same from the main body, wherein the peel device is vertically downwardly movable upon application of an impact thereto.

With the peel device having the above structure, in which an impact is applied to the peel device which is brought into contact with the adherend such that the peel device vertically downwardly moves to peel off the adherend from the main body, for example, when an impact is applied by dropping a rigid body, the impact is transferred to the adherend via the peel device such that the impact can be stably applied to a predetermined position of the adherend (a contact portion between the peel device and the adherend). Whereby, stable test results can be obtained without influences of, such as the position to which an impact is applied, the shape of the rigid body or the impact area.

In the peel tester of the present invention, it is preferable that the load detection device and the displacement detection device each are provided in pair; the pair of the load detection devices each have a leading end to which the adherend is adhered via an adhesive tape; and the peel device is installed at a middle portion between the pair of the load detection devices.

With the peel tester having the above structure, the peel device is installed at a middle portion between the pair of the load detection devices such that the contact portion of the peel device with the adherend is located at a middle portion between the adhering positions of the pair of the load detection devices with the adherend. With this, when the adherend is peeled off, the load is evenly applied to the adhesive tape adhered to the pair of the load detection devices such that variation in change of the load detected by the pair of the load detection devices can be limited.

In the peel tester of the present invention, it is preferable that the main body further includes a guide member that guides the peel device vertically downwardly and the one load detection device, wherein with the adherend adhered to a leading end of the load detection device, the peel device is brought into contact with the adherend through its positions symmetrical to each other about the load detection device.

With the peel tester having the above structure, wherein the main body further includes a guide member that guides the peel device vertically downwardly; and with the adherend adhered to a leading end of the one load detection device via the adhesive tape, the peel device is brought into contact with the adherend through its positions symmetrical to each other about the load detection device, it is possible to improve the test accuracy in performing a peel test.

Specifically, when the peel device is moved vertically downwardly by an impact in a peel test, it is moved while being guided by the guide member, which can prevent variation in the applying direction of the load applied to the adherend so as to achieve effective load application to the adherend under stable conditions. Furthermore, since the peel device is brought into contact with the adherend through its positions symmetrical to each other about the load detection device, such that the load can be applied to the adherend with good balance. Whereby, even when a peel test is repeatedly performed, it is possible to restrain variation in load applied to the adherend, and stably detect change in load detected by the load detection device.

In the peel tester of the present invention, it is preferable that the guide member guides the adherend vertically downwardly when the adherend is peeled off from the main body.

With the peel tester having the above structure, wherein the adherend is guided vertically downwardly by the guide member when it is peeled off from the main body, the peeling direction of the adherend can be stably oriented to the vertically downward direction. Whereby, it is possible to effectively transfer the load applied in the vertically downward direction by the peel device to the adherend, such that it is possible to more stably detect change in load applied to the adherend.

According to the present invention, there is further provided a method for evaluating impact peel characteristics of an adhesive tape by applying an impact to an adherend adhered to a main body via the adhesive tape to peel off the adherend, including detecting change in load applied to the adhesive tape by a load detection device until the adherend is peeled off from the main body, detecting change in moving distance of the adherend by a displacement detection device until the adherend is peeled off from the main body; and integrating the change of the load with respect to the change of the moving distance, thereby evaluating the impact peel characteristics of the adhesive tape.

By the method for evaluating peel characteristics of an adhesive tape having the above steps, it is possible to continuously and quantitatively keep track of the change of the load applied to the adhesive tape by an impact and the change of the moving distance of the adherend corresponding to this change of the load. Furthermore, it is possible to quantitatively keep track of the energy applied to the adhesive tape until the adherend is peeled off by the impact and quantitatively evaluate the impact peel characteristics of the adhesive tape by integrating the change of the load with respect to the change of the moving distance.

According to the present invention, there is further provided an adhesive tape tested by any one of the above peel testers. There is still further provided a mobile device including a liquid crystal display part fixed in position by using the adhesive tape tested by any one of the above peel testers.

Advantages of the Invention

According to the present invention, it is possible to continuously detect the characteristics of an adhesive tape from the moment an impact is applied to an adherend until the adherend is peeled off, as well as quantitatively evaluate the impact peel characteristics of an adhesive tape by using the detected test result.

BRIEF DESCRIPTION OF THE DRAWINGS

FIG. 8(*a*) is a plan view of the peel tester of the fourth embodiment and FIG. 8(*b*) is a cross sectional view taking along a line X-X in FIG. 8(*a*).

FIG. 9 are cross sectional views taken along a line Y-Y in FIG. 8(*a*), in which FIG. 9(*a*) is a view showing a state before a rigid body collides with a peel device, and FIG. 9(*b*) is a view showing a state after the rigid body collides with the peel device.

DETAILED DESCRIPTION OF THE PREFERRED EMBODIMENT

Now, the description will be made for a first embodiment of the present invention with reference to FIGS. 1 to 4.

Figure 1:
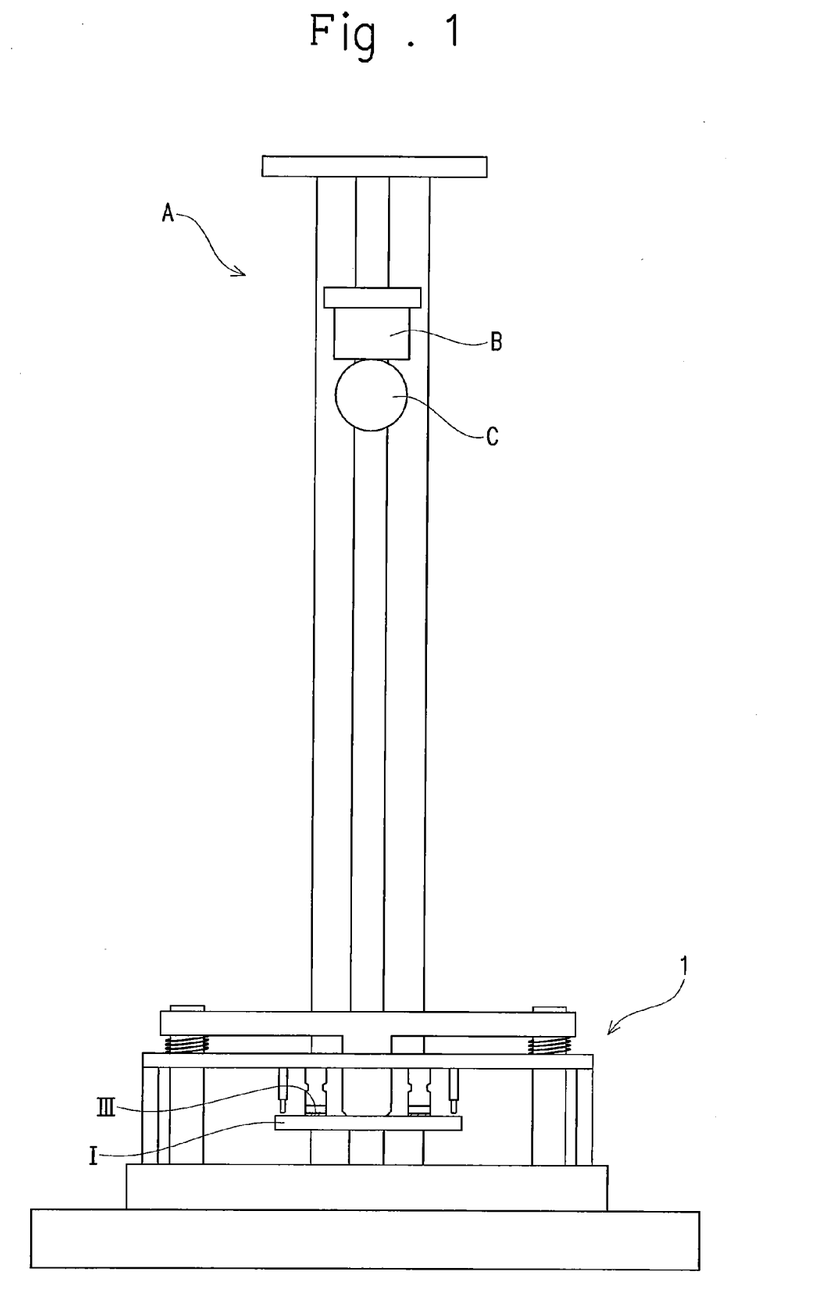
FIG. 1 is a front view of a peel tester of a first embodiment of the present invention in a state where it is installed on a drop tester.

As shown in FIG. 1, a peel tester 1 of the first embodiment is designed to perform a peel test, in which an adherend I is adhered to the peel tester 1 via an adhesive tape III and an impact is applied to the peel tester 1 so as to peel off the adherend I. Although no limitation is intended, as an example of a means for imparting impact, as shown in FIG. 1, a drop tester A that drops a rigid body C from a predetermined height may be used. The drop tester A includes an arm B that lifts the rigid body C up to a predetermined height and has a leading end provided with an electromagnet that temporarily generates a magnetic force when an electrical current runs therethrough. The rigid body C is preferably made of a material that can be attracted by the electromagnet. For example, a steel ball made of a steel material may be used.

The rigid body C is adhered to a leading end of the arm B where a magnetic force has been generated, then is lifted up to a predetermined height and then is dropped by cutting off the magnetic force. The dropped rigid body C collides with the peel tester 1 to have the adherend I peeled off from the peel tester 1 by an impact generated at this moment.

Figure 2:
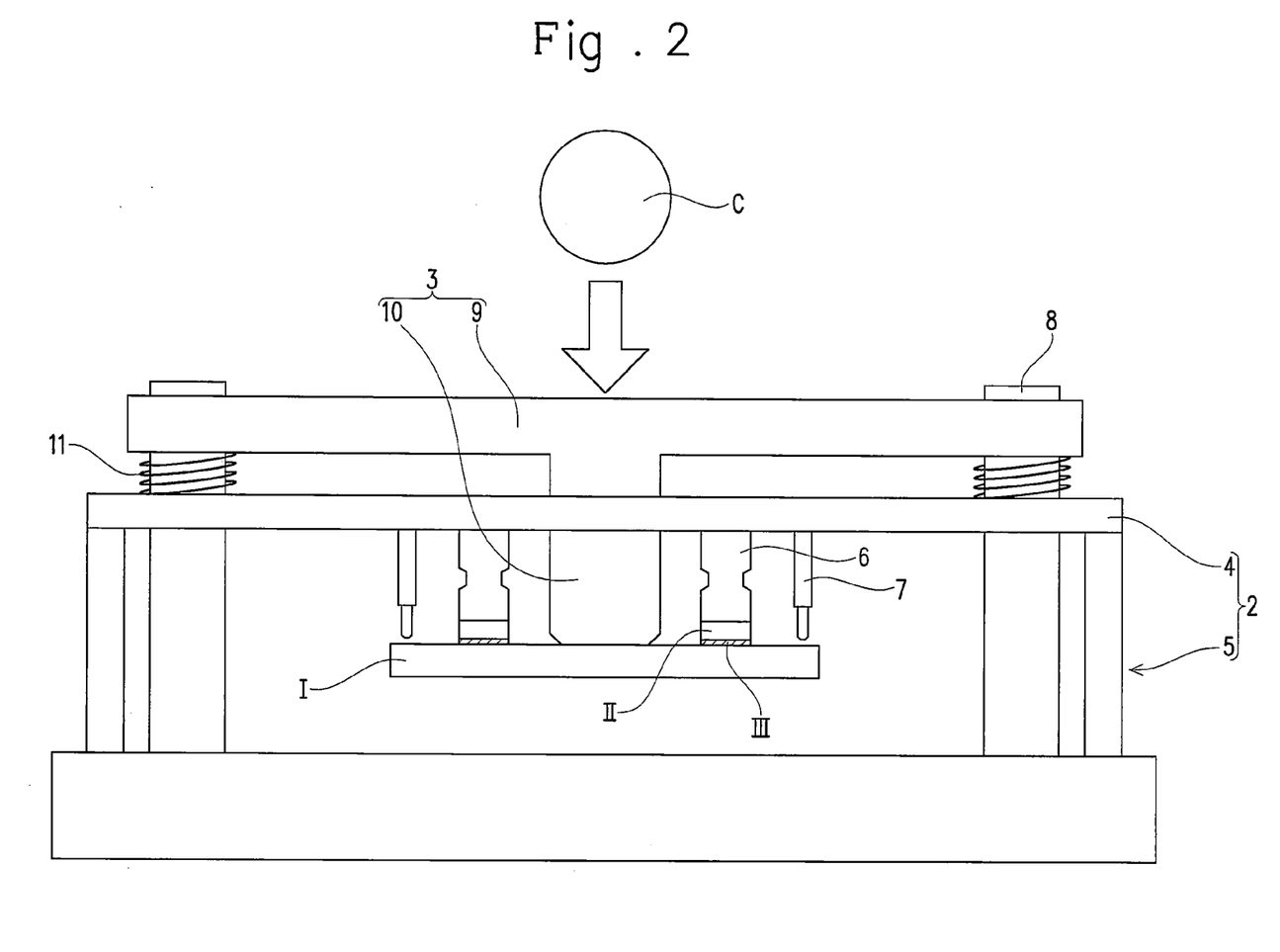
FIG. 2 is a front view of the peel tester of the first embodiment.
Figure 3:
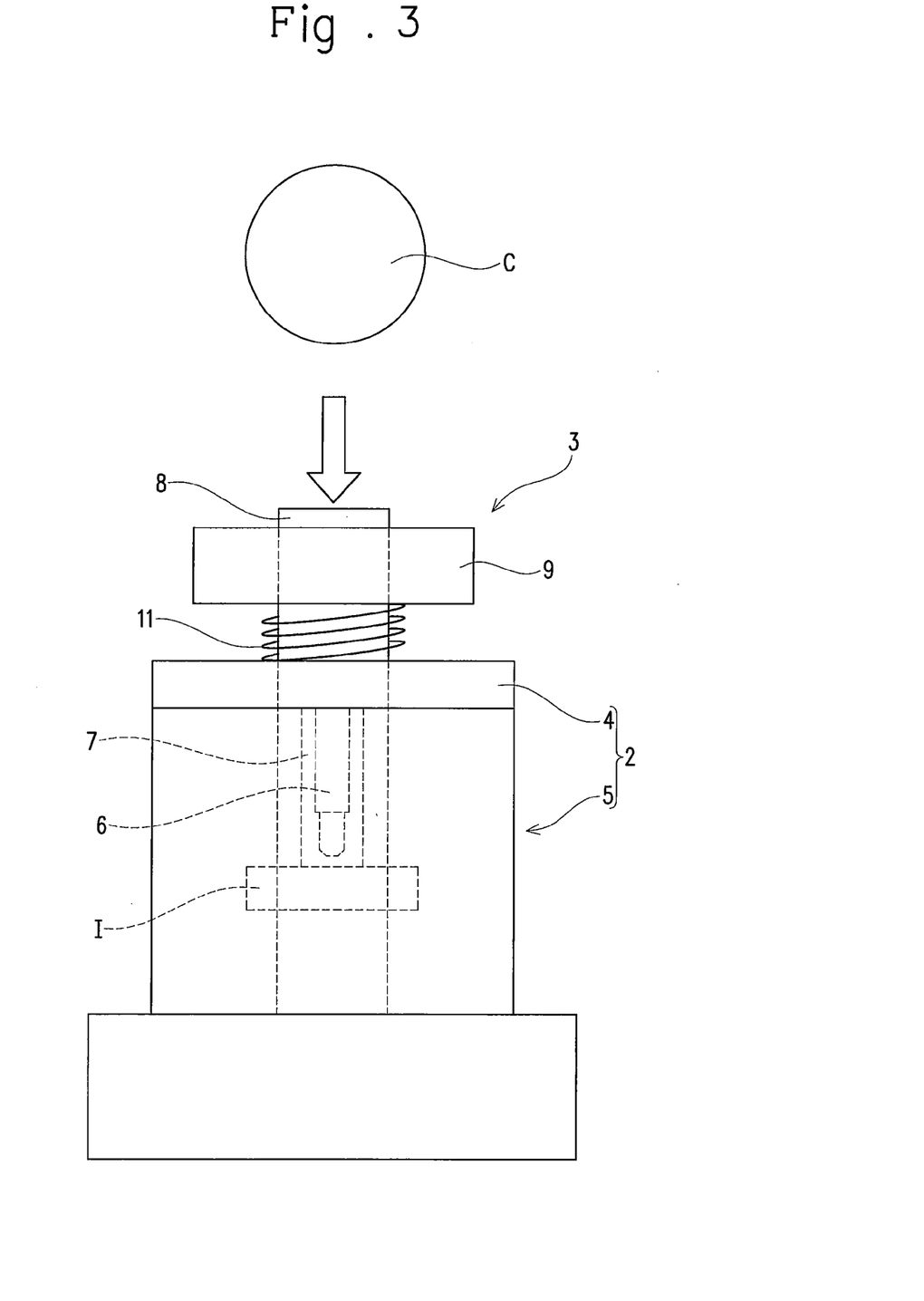
FIG. 3 is a side view of the peel tester of the first embodiment.

The peel tester 1 includes a main body 2 to which the adherend I is adhered via the adhesive tape III, as shown in FIGS. 2 and 3. The peel tester 1 includes a peel device 3 that peels off the adherend I from the main body 2.

The main body 2 includes load detection devices 6 that detect change in load applied to the adhesive tape III until the adherend I is peeled off from the main body 2, and displacement detection devices 7 that detect moving distance of the adherend I until the adherend I is peeled off from the main body 2. Specifically, the main body 2 is made up of a detection device fixing part 4 having the load detection devices 6 and the displacement detection devices 7 fixed thereto, and a base part 5 that supports the detection device fixing part 4.

The detection device fixing part 4 is structured to be detachably attached to the base part 5. Specifically, the detection device fixing part 4 has opposite ends detachably fixed to an upper end of the base part 5. The detection device fixing part 4 has an opening at its center through which the peel device 3 is insertable. The detection device fixing part 4 has a single plate shape. Specifically, the detection device fixing part 4 has a rectangular plate shape, and has upper and lower sides having smooth surfaces formed in parallel to each other.

The detection device fixing part 4 is also structured so as not to be deformed by an impact applied to the adherend I. Specifically, the detection device fixing part 4 is made of a rigid material. As a rigid material, it is preferable to use a material, for example, a metal material such as iron, steel or copper, which is hardly bent by a load.

The load detection devices 6 and the displacement detection devices 7 each are provided in pair to the main body 2. Specifically, the load detection devices 6 and the displacement detection devices 7 each are provided in pair at an one end face of the detection device fixing part 4. The pair of the load detection devices 6 each have one end fixed to the detection device fixing part 4 and are disposed in proximity with an opening of the detection device fixing part 4 with the opening held therebetween.

The load detection devices 6 each have an opposite end, to which the adherend I is adhered via the adhesive tape III. Specifically, the load detection devices 6 each are structured to have an opposite end, to which an adherend II is detachably mounted via the adhesive tape III, in which the adherend I is adhered to the adherend II. The thickness of each of the adherends II is optionally changed such that the surface to which the adhesive tape III of the adherend I adhered to the opposite end of the load detection devices 6 is adhered can be leveled.

The load detection devices 6 each are structured to detect change in applied load when the adherend I is peeled off from the main body 2. Specifically, the load detection devices 6 detect change in load applied in a direction in which the adherend I is separated away from the load detection devices 6. Although no limitation is intended, as the load detection devices 6, strain indicators for detecting the strain due to the load may be used, and preferably tension-type piezoelectric load cells are be used.

The pair of the displacement detection devices 7 are respectively disposed in proximity with the pair of the load detection devices 6. Specifically, the pair of the displacement detection devices 7 are disposed outward of the pair of the load detection devices 6 with the opening therebetween. The displacement detection devices 7 each have a proximal end fixed to the detection device fixing part 4.

The displacement detection devices 7 detect change in moving distance of the adherend I in proximity with a position where the load detection devices 6 and the adherend I are adhered together. Specifically, gaps are formed between the leading ends of the displacement detection devices 7 and the adherend I adhered to the load detection devices 6, and the displacement detection devices 7 detect change in these gaps. The change in gap corresponds to the stretching amount of an adhesive coated on the adhesive tape III. Although no limitation is intended, as the displacement detection devices 7, capacitance displacement meters or laser displacement meters may be used.

The base part 5 has an upper end to which the detection device fixing part 4 is detachably fixed. Specifically, the base part 5 is installed with the one end face (a detection device fixing face) thereof facing downward, and is detachably fixed to both ends of the detection device fixing part 4. The base part 5 includes peel device 3 mounting parts 8 for mounting the peel device thereto.

The peel device mounting parts 8 are respectively formed at the opposite longitudinal ends of the base part 5. The peel device mounting parts 8 each have a columnar shape extending upward along the vertical direction from the base part 5, and structured to extend through the longitudinal end portions of the detection device fixing part 4 with the detection device fixing part 4 held mounted to the base part 5. The peel device mounting parts 8 respectively include spring members 11 for supporting the weight of the peel device 3 at a portion upward of the detection device fixing part 4 with the detection device fixing part 4 held mounted to the base part 5.

The peel device 3 is mounted to the main body 2 when in use. The peel device 3 moves downward in the vertical direction by the collision of the rigid body C, and is brought into contact with the adherend I, thereby peeling the same off from the main body 2. Specifically, the peel device 3 includes a rigid body collision part 9 with which the rigid body C collides and a contact part 10 that is brought into contact with the adherend I. The rigid body collision part 9 includes a collision surface on its upper side, with which the rigid body C collides, and openings, through which the peel device mounting parts 8 are insertable. Specifically, the rigid body collision part 9 is formed by using a rectangular plate member, and has openings at the opposite longitudinal ends, through which the peel device mounting parts 8 are insertable.

The contact part 10 is disposed at the center portion of the rigid body collision part 9. Specifically, the contact part 10 is disposed at the center portion between the two openings through which the peel device mounting parts 8 are inserted, and has a columnar shape extending vertically downwardly from a lower side (a side opposite to the impact side) of the rigid body collision part 9. The contact part 10 is formed to be insertable into the opening formed at the center portion of the detection device fixing part 4 (the middle portion between the pair of the load detection devices 6).

Now, the description will be made for the procedures to perform a test using the peel tester having the above structure.

First, the adherend I is adhered to the main body 2 via the adhesive tape III. Specifically, the detection device fixing part 4 is detached from the base part 5 and positioned to have the side, on which the load detection devices 6 and the displacement detection devices 7 are provided, facing upward, and then the adherend II is fixed to the leading ends of the pair of the load detection devices 6. As a fixing manner, the adherend II may be fixed by using, for example, screws or bolts.

Then, the adhesive tape III is adhered to the upper side of the adherend II, and then the adherend I is laid thereon. A predetermined weight is applied through the upper side of the adherend I and they are cured for a predetermined time. Although no limitation is intended, as an example of the curing method, the curing may be achieved by applying a load of 2 kg for 10 minutes.

Herein, as the adherend I to be adhered, an adherend having a predetermined shape and a constant thickness is preferably used for the purpose of limiting scattering of the test results. Specifically, the adherend I is made up using a plate member having a rectangular shape. As the position to which the adhesive tape III is adhered, for example, when the adherend I has a rectangular shape, the adhesive tape III is preferably adhered to the opposite longitudinal ends of the adherend I. Although no limitation is intended, as the material of the adherends I and II, metal materials such as stainless steel and aluminium, and resin materials such as an acrylic resin and a polycarbonate resin may be used.

Then, the detection device fixing part 4 with the adherend I adhered thereto is mounted to the base part 5. Specifically, the detection device fixing part 4 is mounted to have its side with the adherend I adhered thereto (the side with the load detection devices 6 and the displacement detection devices 7 provided thereon) facing downward. Whereby, the adherend I is adhered to the main body 2 with the side with the adhesive tape III adhered thereto facing upward.

Then, the peel device 3 is mounted to the main body 2. Specifically, the peel device mounting parts 8 are inserted into the openings formed at the opposite ends of the rigid body collision part 9, and the contact part 10 is inserted into the opening formed at the center potion of the detection device fixing part 4 and mounted in position. Whereby, the peel device 3 is installed at the intermediate position of the pair of the load detection devices 6, such that the leading end of the contact part 10 is brought into contact with the center portion of the side of the adherend I to which the adhesive tape III is kept adhered.

The peel device 3 is mounted to the main body 2 so as not to have the weight of the peel device 3 applied to the adherend I. Specifically, the spring members 11 provided to the peel device mounting parts 8 are located between the peel device 3 and the detection device fixing part 4 so as to support the weight of the peel device 3 to prevent application of the weight to the adherend I.

The weight of the peel device 3 may be supported by a friction force between the peel device 3 and the peel device mounting parts 8 without providing the spring members 11. Specifically, the openings formed at the opposite ends of the peel device 3 are formed slightly larger than the cross sectional shapes of the peel device mounting parts 8 to constantly hold the peel device mounting parts 8 in contact with the openings when the peel device mounting parts 8 are placed in the openings, thereby causing a friction force between the peel device 3 and the peel device mounting parts 8 so as to support the weight of the peel device 3.

Although no limitation is intended, as a method for confirming that the weight of the peel device 3 is not being applied to the adherend I, a sheet (Prescale manufactured by Fujifilm Corporation) that changes color due to the applied load is attached to the contact interface between the adherend I and the contact part 10 to confirm that it does not change color, or such confirmation may be achieved based on the detected values of piezoelectric load cells for use as the load detection devices 6.

The peel device 3 thus mounted is brought into contact with the adherend I to be subjected to impact, thereby moving vertically downwardly so as to peel off the adherend I from the main body 2. Specifically, the rigid body C dropped from a predetermined height collides with the rigid body collision part 9, causing an impact which in turn causes the peel device 3 to be guided by the peel device mounting parts 8 and moved vertically downwardly. Whereby, the contact part 10 applies the load onto the side of the adherend I with the adhesive tape III adhered thereto, and peels off the adherend I from the main body 2.

At this moment, the pair of the load detection devices 6 detect change in load applied to the adhesive tape III from the moment of application of the load to the adherend I until peeling off of the adherend I. Also, the pair of the displacement detection devices 7 detect change in moving distance of the adherend I from the moment of application of the load to the adherend I until peeling off of the adherend I (change in spacing between the displacement detection devices 7 and the adherend I). Thus, according to the pair of the load detection devices 6 and the pair of the displacement detection devices 7, the test results at the two points of the adherend I can be obtained by a single impact. By the use of the average of the test results of these two points, evaluation on the peel characteristics mentioned below is made so as to average variations of the test results due to the difference in position to which an adhesive tape is adhered, and hence achieve the accurate evaluation.

Figure 4:
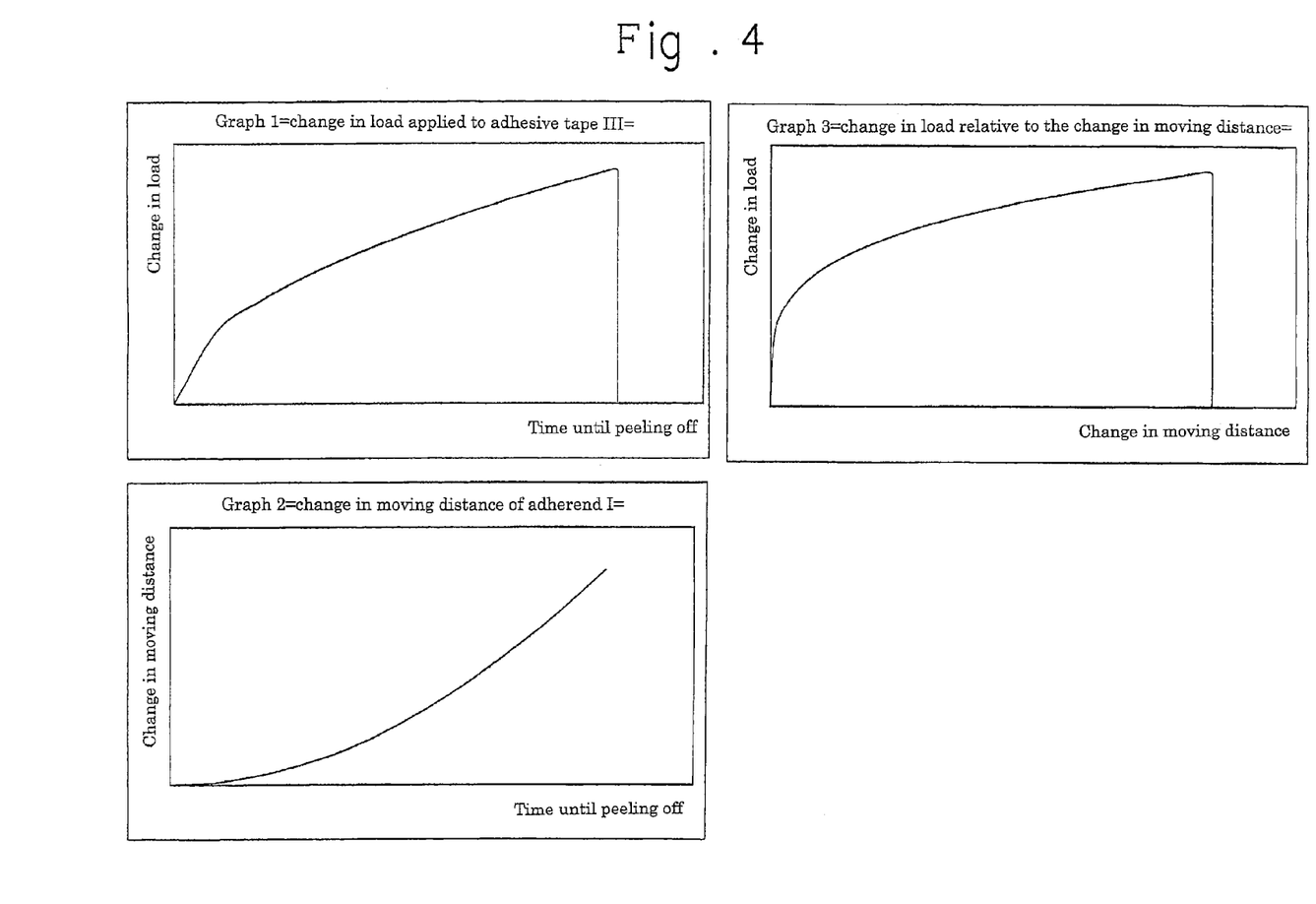
FIG. 4 is graphs of the test results obtained by the peel tester of the first embodiment.

Now, the description will be made for the method for evaluating the peel characteristics of the adhesive tape III according to the impact by the use of the test results of the load detection devices 6 and the displacement detection devices 7, with reference to FIG. 4.

First, the test result by the load detection devices 6 can be obtained as change in load relative to the elapse of the time from the moment of application of the load to the adhesive tape III until peeling off, as shown in Graph 1. That is, the load just before it becomes zero may be designated as the limit load (stress) of the moment the adherend I is peeled off. Or, in the time immediately before the load becomes zero, by differentiating the change in load, the load (stress) of the moment of peeling off of the adherend I can be found. That is, the limit load applicable to the adhesive tape III can be found.

The test result by the displacement detection devices 7 can be obtained as the change in moving distance of the adherend I relative to the elapse of the time from the moment of application of the load to the adherend I until the peeling off, as shown in Graph 2. The change of the load relative to this moving distance is graphed out so as to obtain a graph as shown in Graph 3. Then, from this graph, the change of the load is integrated with respect to the change of the moving distance such that the total amount of energy applied to the adhesive tape III from the moment of application of the load to the adhesive tape III until the peeling off can be found, and the total amount of energy can be evaluated as the peel characteristics of the adhesive tape III by the impact.

Thus, according to the peel tester 1 of the first embodiment, it is possible to continuously detect the characteristics of an adhesive tape III from the moment of application of an impact to the adherend I until peeling off of the adherend I, as well as quantitatively evaluate the impact peel characteristics of the adhesive tape III by using the detected test results.

That is, the peel tester 1 is made up of the main body 2 to which the adherend I is adhered via the adhesive tape III, and the main body 2 includes the load detection devices 6 that detect change in load applied to the adhesive tape III until peeling off of the adherend I from the main body 2, and the displacement detection devices 7 that detect change in moving distance of the adherend I until peeling off of the adherend I from the main body 2. Thus, it is possible to continuously detect change in load from the moment of application of the load to the adherend I until peeling off. For example, in a peel test performed to peel off the adherend I by an impact resulting from collision of the rigid body C, even when an instantaneous impact due to the collision of the rigid body C took place, it is possible to continuously detect change in load applied to the adhesive tape III from the moment of collision of the rigid body C until peeling off of the adherend I. Also, it is possible to continuously detect change in moving distance of the adherend I from the state where the adherend I is kept adhered to the main body 2 until peeling off of the adherend I. For example, in a peel test performed to peel off the adherend I by an impact resulting from the collision of the rigid body C, the adherend I moves in a direction in which an impact is applied to the adherend I (the direction in which the rigid body C is dropped), and then is peeled off from the main body 2. At this moment, it is possible to continuously detect how far the adherend I has moved from the adhered position on the main body 2 up until peeling off.

The peel tester 1 includes the peel device 3 that is brought into contact with the adherend I to peel off the same from the main body 2. The peel device 3 is designed to be movable vertically downwardly upon receiving an impact. Accordingly, by the application of an impact by dropping the rigid body C, the impact is transferred to the adherend I via the peel device 3 such that an impact can be stably applied to a predetermined position of the adherend I (a contact portion between the peel device 3 and the adherend I). Whereby, stable test results can be obtained without influences of, such as the position to which an impact is applied, the shape of the rigid body C or the impact area.

The main body 2 of the peel tester 1 includes a pair of load detection devices 6 and a pair of displacement detection devices 7, in which the pair of the load detection devices 6 each have a leading end to which the adherend I is adhered via the adhesive tape III, and the peel device 3 is installed at the middle portion between the pair of the load detection devices 6. Thus, the contact position between the peel device 3 and the adherend I is located at the middle portion between the adhered positions at which the adherend I is adhered to the pair of the load detection devices 6. With this, when the adherend I is peeled off, the load is evenly applied to the adhesive tape III adhered to the pair of the load detection devices 6 such that variation in change of the load detected by the pair of the load detection devices 6 can be limited.

The evaluation method of the impact peel characteristics of the adhesive tape III is performed by: detecting change in load applied to the adhesive tape III until the adherend I is peeled off from the main body 2 by the load detection devices 6; detecting change in moving distance of the adherend I until the adherend I is peeled off from the main body 2; integrating the change of the load with respect to the change of the moving distance to thereby evaluate the impact peel characteristics of the adhesive tape III. Thus, it is possible to continuously and quantitatively keep track of the change of the load applied to the adhesive tape III by the impact and the change of the moving distance of the adherend I corresponding to this change of the load. Furthermore, it is possible to quantitatively keep track of the energy applied to the adhesive tape III until the adherend I is peeled off by the impact and thus quantitatively evaluate the impact peel characteristics of the adhesive tape III.

Figure 5:
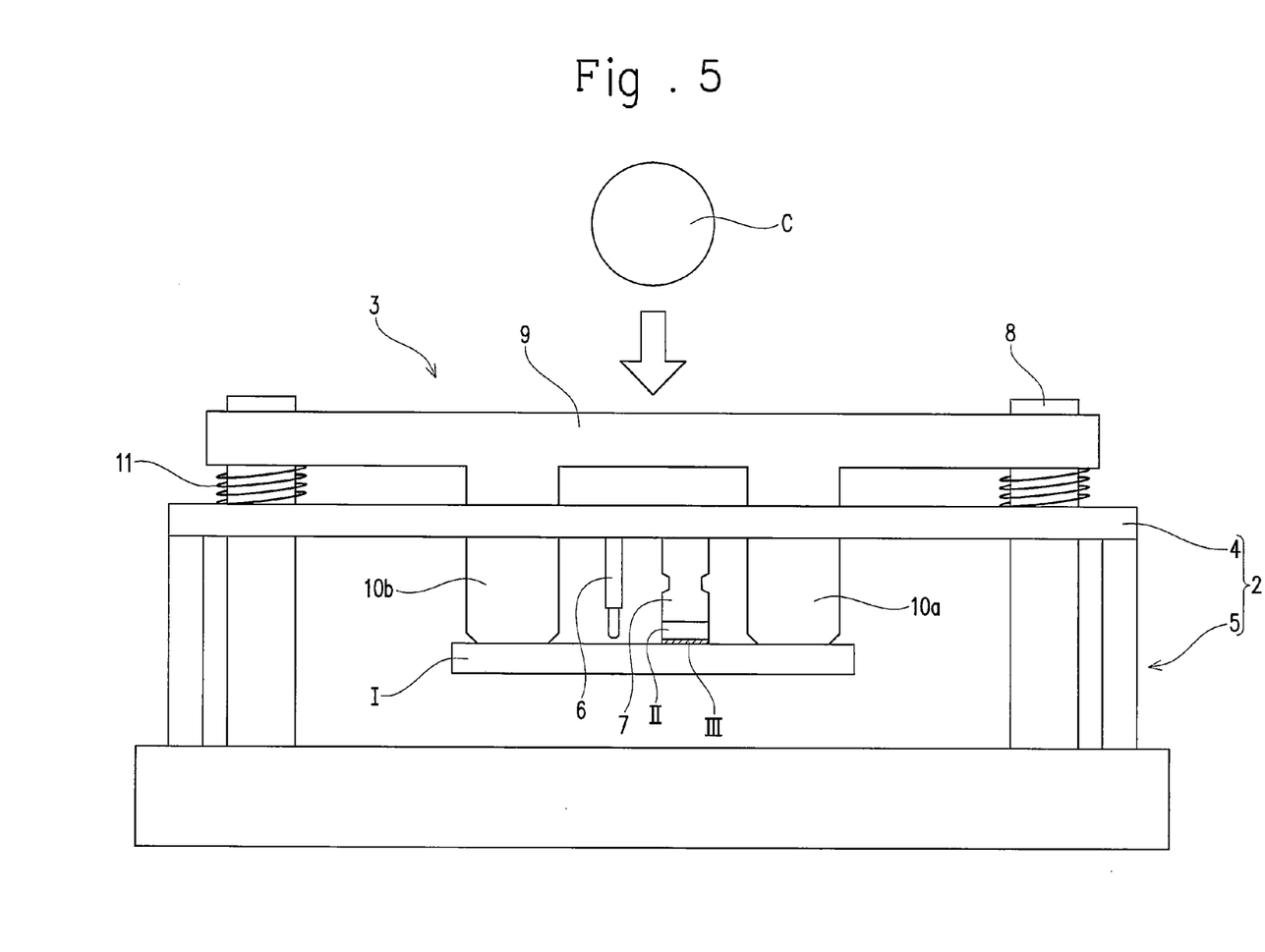
FIG. 5 is a front view of a peel tester of a second embodiment of the present invention.

In the first embodiment, the peel device 3 is structured to bring the contact part 10 into contact with the center portion of the adherend I, but this is not essential. It is possible to have the adherend I contacted through its plural portions. For example, as shown in the second embodiment in FIG. 5, it is possible to employ a structure in which contact parts 10a, 10b are brought into contact with the opposite ends of the adherend I. With this structure, an impact applied to the peel device 3 can be transferred to the entire area of the adherend I and scattering of the test results caused by the distortion of the adherend I can be suppressed.

Figure 6:
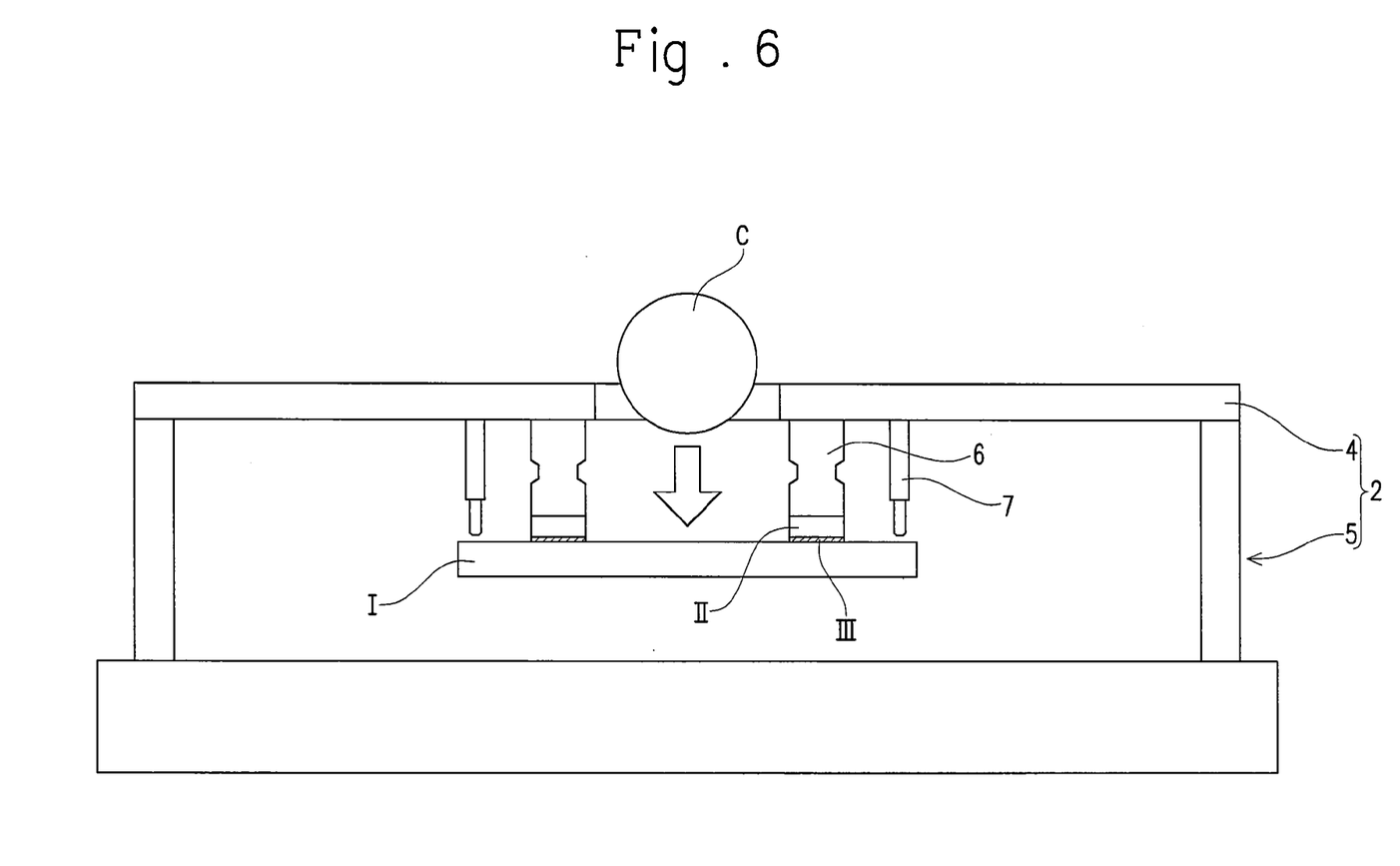
FIG. 6 is a front view of a peel tester of a third embodiment of the present invention.

In the first embodiment, the adherend I is peeled off from the main body 2 by the peel device 3, but this is not essential. The impact may be applied directly to the adherend I by an impact applying means. For example, as shown in the third embodiment in FIG. 6, it is possible to employ a structure in which the rigid body C dropped from a predetermined height directly collides with the adherend I to apply an impact thereto. With this structure, the impact force can be transferred to the adherend I without loss of the force to be applied to the adherend I such that more accurate test results can be obtained.

Figure 7:
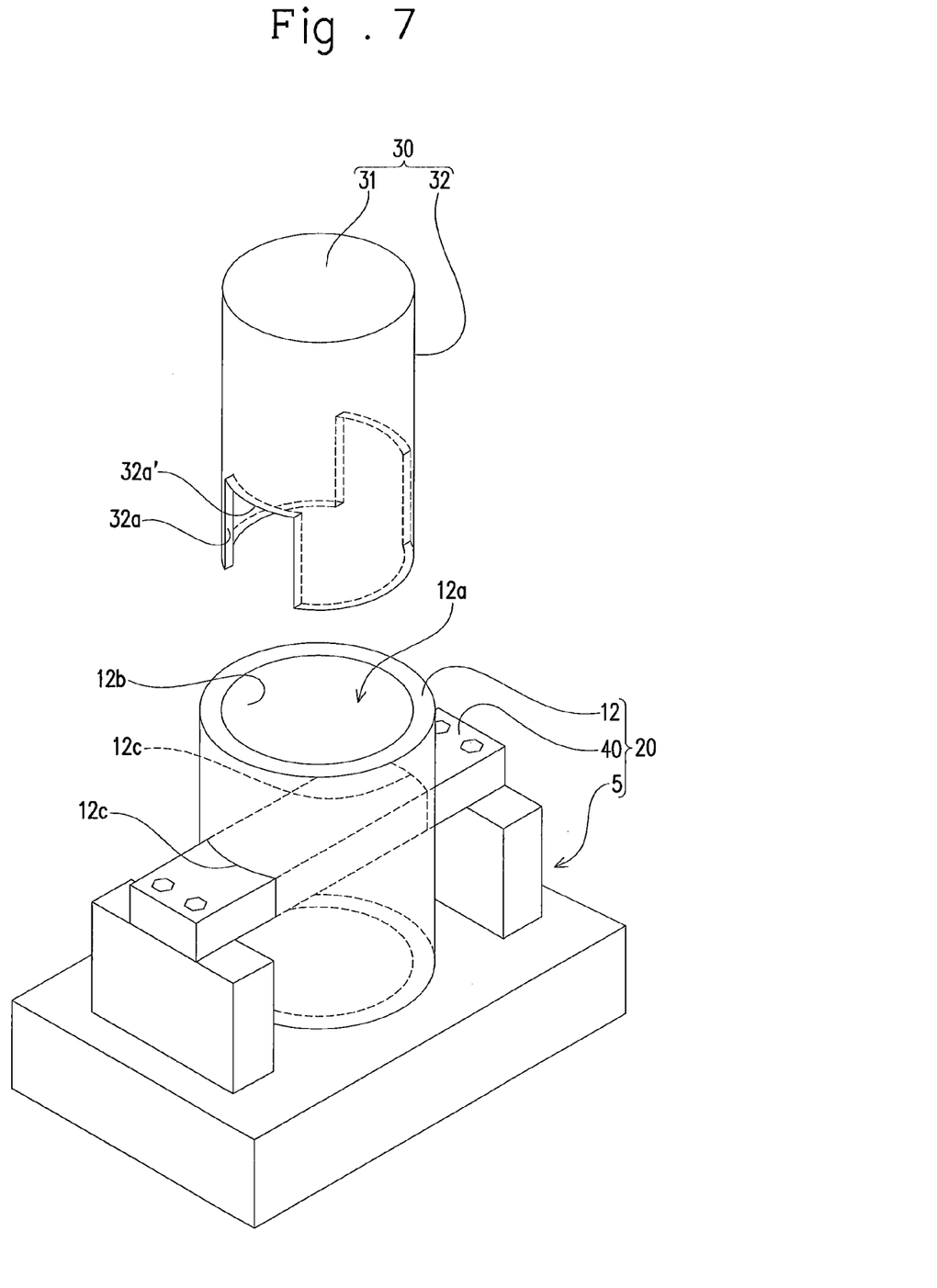
FIG. 7 is a perspective view of a peel tester of a fourth embodiment of the present invention.
Figure 8A:
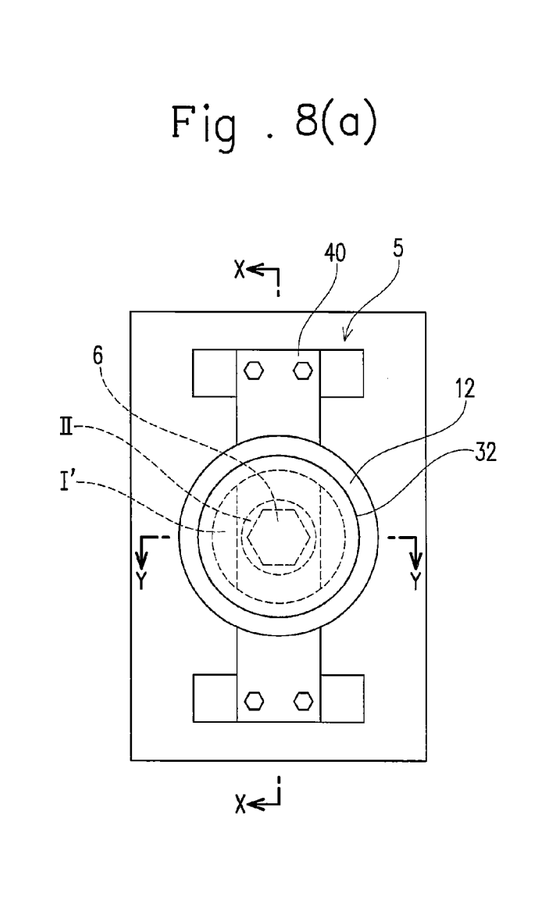
Figure 8B:
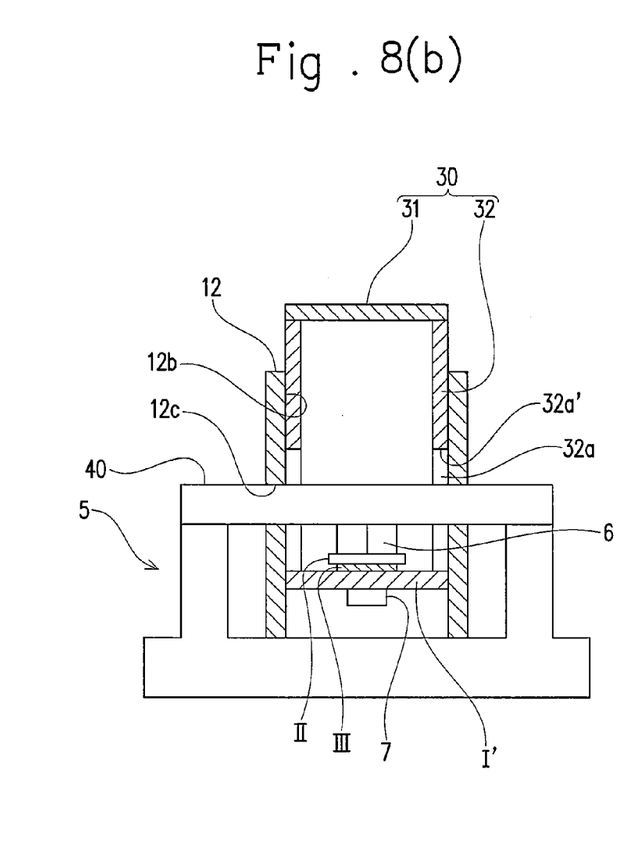

Now, the description will be made for a fourth embodiment of the present invention with reference to FIGS. 7 to 9. The peel tester 1 of the fourth embodiment is different from that of the first embodiment mainly in the structure of a main body 20 and the structure of a peel device 30 corresponding thereto. Thus, the following description will be mainly made for the differences relative to the first embodiment with allocating the same reference numbers to the same members or parts to omit the description thereof.

The main body 20 includes a detection device fixing part 40 with load detection devices 6 fixed thereto, a base part 5, and a guide member 12 that guides the peel device 30 in a moving direction. The guide member 12 is structured to allow the peel device 30 to be disposed inside thereof. Specifically, the guide member 12 has a guide hole 12a formed into a straight shape for communication between the opposite ends and is structured to allow the peel device 30 to be disposed inside of the guide hole 12a. Specifically, the guide member 12 has a tubular shape (specifically a hollow columnar shape having a straight profile) having the guide hole 12a at the center portion thereof.

The guide member 12 with the peel device 30 held disposed therein is structured to slidingly contact the peel device 30. Specifically, the guide member 12 has a guide surface 12b defining the guide hole 12a, such that, with the peel device 30 held disposed in the guide hole 12a, the guide surface 12b slidingly contacts the outer circumference of the peel device 30. The guide surface 12b has a shape corresponding to the shape of the outer circumference of the peel device 30 (specifically, a hollow columnar shape). The guide hole 12a is defined by the space (specifically, the columnar space) encompassed by the guide surface 12b.

The guide member 12 is disposed so as to cross the detection device fixing part 40. Specifically, the guide member 12 has a pair of through-holes 12c extending in a direction crossing the axis of the guide hole 12a (specifically, in a direction substantially orthogonal thereto), in which the detection device fixing part 40 is inserted through the pair of the through-holes 12c such that the detection device fixing part 40 extends through the guide member 12.

The pair of the through-holes 12c are formed symmetrically about the axis of the guide hole 12a, and with the detection device fixing part 40 held inserted therethrough, the detection device fixing part 40 is arranged substantially orthogonal to the axis of the guide hole 12a. With this, when the guide member 12 is arranged so as to have the axial direction of the guide member 12 (specifically, the axial direction of the guide hole 12a) oriented in the vertical direction, the detection device fixing part 40 inserted through the pair of the through-holes 12c is oriented in a substantially horizontal plane, and oriented at substantially right angle relative to the moving direction (i.e., vertically downward direction) of the peel device 30.

Meanwhile, the peel device 30 is structured to be able to be disposed inside of the guide member 12. Specifically, the peel device 30 is formed to be able to be disposed inside of the guide hole 12a and to be held in sliding contact with the guide surface 12b. More specifically, the peel device 30 includes a rigid body collision part 31 with which the rigid body C collides and a sliding contact part 32 that is connected to the rigid body collision part 31 and slidingly contacts the guide surface 12b.

The rigid body collision part 31 has a plate shape and is located at one end of the peel device 30. Specifically, the rigid body collision part 31 is located at one end of the peel device 30 so as to extend substantially orthogonal to the axis of the guide hole 12a when the peel device 30 is held disposed inside of the guide member 12. With this, when the guide member 12 has been disposed with the axis of the guide hole 12a extending in the vertical direction, an impact force of the rigid body C which has collided with the rigid body collision part 31 is effectively transferred in the axial direction of the guide hole 12a (i.e., in the vertically downward direction).

The rigid body collision part 31 has a shape corresponding to the cross sectional shape of the cylindrically shaped guide surface 12b. Specifically, the rigid body collision part 31 has a circular shape in plan view having an area slightly smaller than the cross sectional area of the guide surface 12b having a hollow columnar shape.

The sliding contact part 32 is formed to conform to the guide surface 12b when the peel device 30 is held inside of the guide member 12. Specifically, the sliding contact part 32 has a tubular shape (more specifically, a hollow columnar shape) so as to conform to the guide surface 12b. The sliding contact part 32 is formed to have a cross sectional shape corresponding to the cross sectional shape of the tubular shaped guide surface 12b. Specifically, the cross sectional shape of the sliding contact part 32 has an area slightly smaller than the cross sectional shape of the tubular shaped guide surface 12b such that the outer circumference of the sliding contact part 32 slidingly contacts the guide surface 12b.

The sliding contact part 32 has one end (first end) (i.e., one end of the peel device 30) connected with the rigid body collision part 31. Specifically, the sliding contact part 32 is connected to an peripheral end of the rigid body collision part 31 so as to extend orthogonal to the plate shaped rigid body collision part 31. More specifically, the sliding contact part 32 is formed into a hollow columnar shape conforming to the peripheral end of the rigid body collision part 31 having a circular shape in plan view. That is, the peel device 30 has a columnar shape conforming to the peripheral end of the guide surface 12b having the hollow columnar shape.

The peel device 30 has another end (second end) (another end opposite to the first end of the sliding contact part 32), which is formed to be capable of fittingly engaging with the detection device fixing part 40. Specifically, the peel device 30 has fitting grooves 32a at the second end structured to be fittingly engageable with the detection device fixing part 40. The fitting groove 32a is structured to be capable of fittingly receiving the detection device fixing part 40 along the rigid body collision part 31. Specifically, the fitting grooves 32a are formed by cutting out in U-shape the second end of the sliding contact part 32 having a hollow columnar shape at portions symmetrical about the axis of the sliding contact part 32. In other words, the fitting grooves 32a are formed at positions symmetrically about the axis of the sliding contact part 32 to each have a U-shape open to the outside towards the second end (i.e. vertically downward direction).

The depth of the fitting grooves 32a is set so as to allow the entire cross sectional profile of the detection device fixing part 40 to be placed within the fitting grooves 32a when the detection device fixing part 40 is held fitted in the fitting grooves 32a. More specifically, at the position at which the detection device fixing part 40 is held in contact with bottom portions 32a' of the fitting grooves 32a, the second end of the peel device 30 (i.e., the second end of the sliding contact part 32) projects outward than the detection device fixing part 40.

The detection device fixing part 40 is disposed horizontally on the base part 5. Specifically, the detection device fixing part 40 is disposed on the base part 5 so as to be oriented in a horizontal plane at the height at which the pair of the through-holes 12c are located, when the guide member 12 has been disposed on the base part 5 with its axis oriented in the vertical direction. The detection device fixing part 40 is structured to allow the load detection devices 6 to be located within the guide member 12 (i.e., within the guide hole 12a) when it extends through the guide member 12. Specifically, the detection device fixing part 40 has a bar shape with its substantially longitudinal center portion to which one load detection device 6 is fixed, such that the load detection device 6 is located in line with the axis of the guide hole 12a when the it extends through the guide member 12.

Before the description on the procedures of a peel test using the peel tester 1 of this embodiment, the description will be made for an adherend I' for use in the peel tester 1 of this embodiment. The adherend I' is vertically downwardly guided when it is peeled off from the position at which it is adhered to the main body 20. Specifically, the adherend P is formed to be placed within the guide member 12 when it is held adhered to the main body 20, as shown in FIG. 8. More specifically, the adherend P has a plate shape (specifically, a disc shape) corresponding in shape to the cross sectional shape of the tubular shaped guide surface 12b, and has an outer circumference slidingly contacting the guide surface 12b when the adherend P is held disposed within the guide hole 12a (is held adhered to the main body 20 via the adhesive tape III).

The adherend I' is provided with a displacement detection device 7. Although no limitation is intended, as the displacement detection device 7, an acceleration sensor (a capacitance type, etc.) is preferably used. Although no limitation is intended to the mounting position of the displacement detection device 7, the displacement detection device 7 is preferably mounted to a region of the surface of the adherend I' opposite to the surface of the same to which the adhesive tape III is to be adhered (specifically, a substantially center portion of the adherend I' in plan view).

When a peel test is to be performed using the above adherend I', the adhesive tape III is first adhered to the adherend II removed from the load detection device 6, and then the adherend I' and the adherend II are adhered together via the adhesive tape III. At this moment, the adherend II is preferably located at a substantially center portion of the adherend I' in plan view. Then, the adherend II is mounted to the load detection device 6 located within the guide member 12 (specifically, within the guide hole 12a). Whereby, the adherend I' is located within the guide hole 12a and below the detection device fixing part 40, while at the same time being held in sliding contact with the guide surface 12b. At this position, the adherend I' is oriented substantially at a right angle relative to the guide surface 12b, and the center of the disc-shaped adherend P is located in line with the axis of the guide hole 12a.

Then, the peel device 30 is disposed inside of the guide hole 12a from above the guide member 12. At this moment, the peel device 30 (specifically, the second end of the peel device 30) is brought into contact with the portions of the adherend I' symmetrical to each other about the load detection device 6. That is, the center portions, of the load detection device 6 and the adherend I' are located in line with the axis of the cylindrically shaped sliding contact part 32. With this positioning, the sliding contact part 32 slidingly contacts the guide surface 12b, while at the same time the detection device fixing part 40 is held in fitted engagement with the fitting grooves 32a and the second end of the peel device 30 is brought into contact with the adherend I' from above (i.e., onto the surface with the adhesive tape III adhered thereto). Whereby, the second end of the peel device 30 having a hollow columnar shape other than the region in which the fitting grooves 32a are formed is held in contact with the outer peripheral edge of the adherend I'.

Figure 9A:
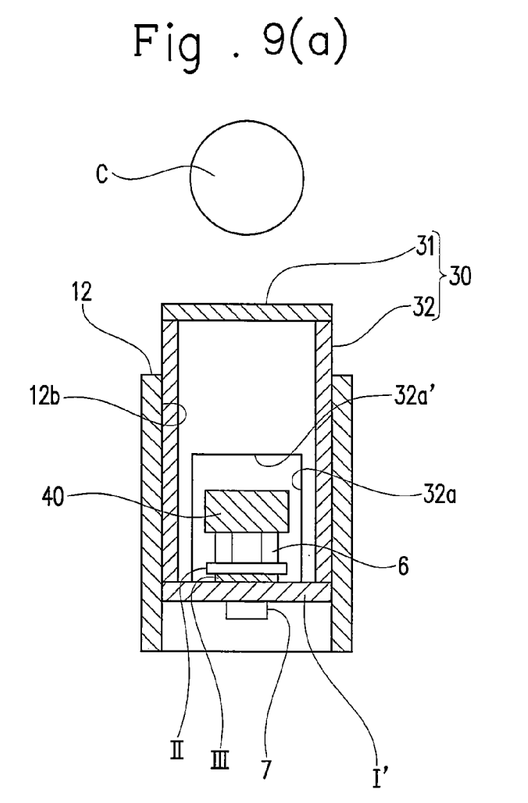
Figure 9B:
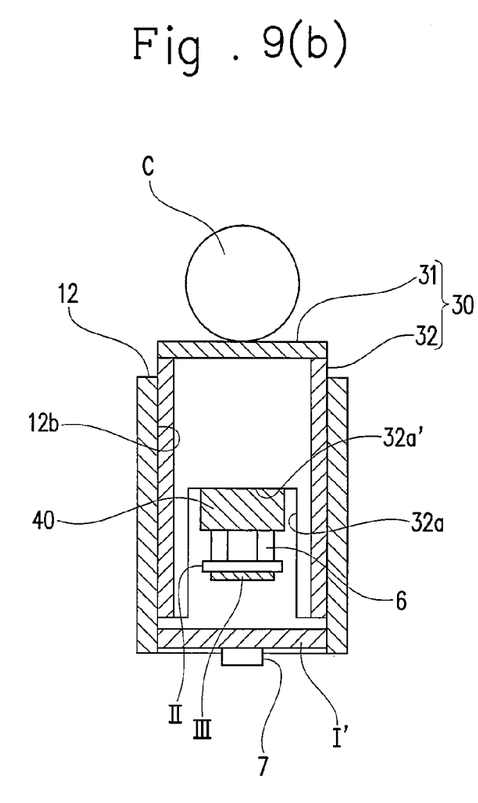

As shown in FIG. 9, the rigid body C is dropped from above the peel device 30 to be collided with the rigid body collision part 31. Whereby, the peel device 30 is moved vertically downwardly along the axis of the guide member 12 (in other words, along the guide surface 12b), thereby peeling off the adherend I' from the adherend II. The peel device 30 stops at the position at which the detection device fixing part 40 is held in contact with the bottom portions 32a' of the fitting grooves 32a. Whereby, the change in load applied to the adherend I' is detected by the load detection device 6, and the numerical value corresponding to the displacement amount of the adherend I' is detected by the displacement detection devices 7.

As described above, according to the peel tester 1 of the fourth embodiment, when the peel device 30 is moved vertically downwardly by an impact in a peeling test, this movement is made while being guided by the guide member 12, which can suppress variation in the applying direction of the load applied to the adherend I' so as to achieve effective load application under stable conditions. Since the peel device 30 is brought into contact with the portions of the adherend I' symmetrical to each other about the load detection device 6, the load can be applied to the adherend I' with good balance. Whereby, even when a peel test is repeatedly performed, variation in load applied to the adherend I' can be suppressed, and the change in load detected by the load detection device 6 can be stably detected, such that the test accuracy in performing a peel test can be further improved.

According to the peel tester 1 of the fourth embodiment, in which the adherend I' is guided vertically downwardly by the guide member 12 when it is peeled off from the main body 20, the peeling direction of the adherend I' can be stably oriented to the vertically downward direction. Whereby, the load applied in the vertically downward direction by the peel device 30 can be effectively transferred to the adherend I', and the change in load applied to the adherend can be more stably detected.

The peel tester 1 of the fourth embodiment is different from that of the first embodiment in that the adherend I' is adhered to the one load detection device 6. Therefore, the adherend II can be mounted to the load detection device 6 while being held adhered to the adherend I' via the adhesive tape III, which enables efficient performance of tests. Specifically, when the adherend II is mounted to the load detection device 6 in threaded engagement, unless the adherends II have been respectively mounted to the two load detection devices 6, the adherend I' cannot be adhered in the first embodiment. Because of this, it is difficult to perform a test upon previously preparing plural samples each having an adherend I' and an adherend II adhered together, and therefore when a peel test is to be performed in plural testing environments (e.g., in an environment in which they are cooled in a refrigerator or in an environment in which they are left at room temperature), the peel tester 1 itself must be placed in a desirable testing environment. Contrarily, in the fourth embodiment, the adherend II is allowed to be mounted to the load detection device 6 in threaded engagement while the adherend I' and the adherend II are held in adhered state, such that plural samples each having an adherend I' and an adherend II adhered together are allowed to be prepared and placed in different environments, which are then subsequently mounted to the load detection device 6 for testing. This enables efficient testing.

The peel tester of the present invention is not necessarily limited to the above embodiments, and may be subjected to various modifications without departing from the scope of the present invention.

For example, in the above embodiments, the evaluation on the impact peel characteristics is made after obtaining a test result by the peel tester 1, but this is not necessary. An evaluation device for evaluation of the impact peel characteristics may be provided to the peel tester. Specifically, the evaluation device for evaluation of the impact peel characteristics may be structured to calculate an maximum load applicable to an adhesive tape and the amount of energy applied to an adhesive tape until an adherend is peeled off, on the basis of the change in load obtained by a load detection device and the moving distance obtained by a displacement detection device, and thereby digitize them.

The displacement detection devices 7 are mounted to the main body 2 (specifically, the detection device fixing part 4) in the first to third embodiments, while the one displacement detection device 7 is mounted to the adherend I' in the fourth embodiment. This is not necessary. The displacement detection devices 7 may be mounted to the adherend I in the first to third embodiments, while the one displacement detection device 7 may be mounted to the main body 20 in the fourth embodiment. Alternatively, the displacement detection device(s) 7 may be disposed at position(s) other than the main body 2 or 20, or the adherend I or I'.

Specifically, in the first to third embodiments, the displacement detection devices 7 (capacitance displacement meters or laser displacement meters) are mounted to the main body 2 (specifically, the detection device fixing part 4) so as to detect a gap relative to the adherend I. This is not necessary. In a similar manner to the displacement detection device 7 of the fourth embodiment, the displacement detection device 7 (an acceleration sensor, etc.) may be mounted to the adherend I so as to detect change in acceleration as the displacement amount of the adherend I. Contrarily, as the displacement detection device 7 of the fourth embodiment, a capacitance displacement meter or the like of the first embodiment may be used and this displacement detection device 7 may be mounted to the main body 20 so as to detect the displacement amount of the adherend I'. Alternatively, the displacement detection device(s) 7 of the first to fourth embodiments may be disposed besides the adherend I or I' so as to perform editing video or image, or allow itself to be combined with a laser displacement meter to detect the displacement of the adherend I, or I'.

DESCRIPTION OF THE REFERENCE NUMERALS

1: peel tester, 2, 20: main body, 3, 30: peel device, 4, 40: detection device fixing part, 5: base part, 6: load detection device, 7: displacement detection device, 8: peel device mounting part, 9: rigid body collision part, 10: contact part, 11: spring member, 12: guide member, 12a: guide hole, 12b: guide surface, 12c: through-hole, 31: rigid body collision part, 32: sliding contact part, 32a: fitting groove, 32a': bottom portion, I, I', II: adherend, III: adhesive tape, A: drop tester, B: arm, C: rigid body

The invention claimed is:

1. A peel tester with a main body, to which an adherend is to be adhered via an adhesive tape, for performing a peel test by an impact applied to the adherend, which comprises:
a peel device that is brought into contact with the adherend to peel off the same from the main body, wherein the peel device is vertically downwardly movable upon application of an impact thereto;
a pair of load detection devices that detect change in load applied to the adhesive tape until the adherend is peeled off from the main body; and
a pair of displacement detection devices that detect change in moving distance of the adherend until the adherend is peeled off from the main body,
wherein the pair of the load detection devices each have a leading end to which the adherend is adhered via an adhesive tape; and the peel device is installed at a middle portion between the pair of the load detection devices.

2. A peel tester with a main body, to which an adherend is to be adhered via an adhesive tape, for performing a peel test by an impact applied to the adherend, which comprises:
a peel device that is brought into contact with the adherend to peel off the same from the main body, wherein the peel device is vertically downwardly movable upon application of an impact thereto;
at least one load detection device that detects change in load applied to the adhesive tape until the adherend is peeled off from the main body; and
at least one displacement detection device that detects change in moving distance of the adherend until the adherend is peeled off from the main body,
wherein the main body further comprises a guide member that guides the peel device vertically downwardly, wherein with the adherend adhered to a leading end of the at least one load detection device via an adhesive tape, the peel device is brought into contact with the adherend at two positions, the two positions being symmetrical to each other about the at least one load detection device.

3. The peel tester according to claim 2, wherein the guide member guides the adherend vertically downwardly when the adherend is peeled off from the main body.

4. The peel tester according to claim 2, wherein the at least one load detection device includes only one load detection device.

5. A method for evaluating impact peel characteristics of an adhesive tape by applying an impact to an adherend adhered to a main body via the adhesive tape to peel off the adherend, comprising:
providing a pair of load detection devices and a pair of displacement detection devices, the pair of the load detection devices each having a leading end to which the adherend is adhered via an adhesive tape;
installing a peel device at a middle portion between the pair of the load detection devices;
bringing the peel device into contact with the adherend to peel off the adherend from the main body, wherein the peel device is brought into contact with the adherend by moving the peel device vertically downwardly upon application of an impact thereto;
detecting change in load applied to the adhesive tape by the pair of load detection devices until the adherend is peeled off from the main body;
detecting change in moving distance of the adherend by the pair of displacement detection devices until the adherend is peeled off from the main body; and
integrating the change of the load with respect to the change of the moving distance, thereby evaluating the impact peel characteristics of the adhesive tape.

6. A method for evaluating impact peel characteristics of an adhesive tape by applying an impact to an adherend adhered to a main body via the adhesive tape to peel off the adherend, comprising:
adhering an adherend to a leading edge of at least one load detection device via an adhesive tape;
bringing a peel device into contact with the adherend to peel off the adherend from the main body, the peel device being brought into contact with the adherend by applying an impact to the peel device and guiding the peel device vertically downward with a guide member provided on the main body to contact the adherend at two positions, the two positions being symmetrical to each other about the at least one load detection device;
detecting change in load applied to the adhesive tape by the at least one load detection device until the adherend is peeled off from the main body;
detecting change in moving distance of the adherend by at least one displacement detection device until the adherend is peeled off from the main body; and
integrating the change of the load with respect to the change of the moving distance, thereby evaluating the impact peel characteristics of the adhesive tape.

7. The method for evaluating impact peel characteristics according to claim 6, wherein the at least one load detection device includes only one load detection device.

\* \* \* \* \*